United States Patent [19]

Spitzer

[11] 4,008,229
[45] Feb. 15, 1977

[54] HALO SUBSTITUTED β-LACTAM ANTIBIOTICS
[75] Inventor: Wayne A. Spitzer, Indianapolis, Ind.
[73] Assignee: Eli Lilly and Company, Indianapolis, Ind.
[22] Filed: July 11, 1974
[21] Appl. No.: 487,702
[52] U.S. Cl. .................. 260/243 C; 260/240 A; 260/240 D; 260/239.1; 424/246; 424/271
[51] Int. Cl.² ............................... C07D 501/16
[58] Field of Search ....... 260/243 C, 240 R, 240 A, 260/240 D

[56] References Cited

UNITED STATES PATENTS

| 3,325,543 | 6/1967 | Degener et al. ............... 260/566 |
| 3,658,792 | 4/1972 | Abe et al. .................... 260/239.1 |
| 3,832,347 | 8/1974 | Kukolja et al. ............... 260/239 A |
| 3,843,641 | 10/1974 | Christensen et al. .......... 260/243 C |
| 3,875,146 | 4/1975 | Christensen et al. .......... 260/243 C |
| 3,890,310 | 6/1975 | Sapino, Jr. et al. ........... 260/243 C |

FOREIGN PATENTS OR APPLICATIONS

71/3229  5/1971  South Africa

*Primary Examiner*—Nicholas S. Rizzo
*Assistant Examiner*—Diana G. Rivers
*Attorney, Agent, or Firm*—Walter E. Buting; Everet F. Smith

[57] ABSTRACT

Imino chlorides of 6-aminopenicillanic esters and 7-aminocephalosporanic esters are reacted at a temperature between −80° and −25° C. with a strong base such as an alkali metal amide of a secondary amine and the generated anion is halogenated to provide the corresponding 6- or 7-halo-N(α-haloalkylidene) or N(α-halo-α-arylmethylidene)-6-aminopenicillanic or 7-aminocephalosporanic esters, respectively. The 6-halopenicillins and 7-halocephalosporins are converted to 6-methoxypenicillins and 7-methoxycephalosporins.

4 Claims, No Drawings

HALO SUBSTITUTED β-LACTAM ANTIBIOTICS

BACKGROUND OF THE INVENTION

This invention relates to a process for preparation of 6-halopenicillanic esters and 7-halocephalosporanic esters. These compounds are valuable as intermediates for conversion to 6-methoxypenicillanic esters and 7-methoxycephalosporanic esters. The acids of said methoxy-β-lactam compounds possess desirable antimicrobial properties.

Since the prediction by J. L. Strominger and D. J. Tipper, Amer. J. Med. 39, 708 (1965), that 6-methylpenicillins and 7-methylcephalosporins should have enhanced microbiological activity and the recent discovery of the 7-methoxycephalosporins obtained from the fermentation of Streptomycete organisms by R. Nagarajan, et al., J. Amer. Chem. Soc., 93, 2308 (1971), considerable interest has developed in the synthesis of β-lactam antibiotics having a substituent α to the β-lactam carbonyl of the penicillin and cephalosporin antibiotics.

OBJECT OF THE INVENTION

An object of the present invention is to provide a readily accessible route from 6-acylaminopenicillins and 7-acylaminocephalosporins to the corresponding 6-methoxypenicillin and 7-methoxycephalosporin compounds. It is a further object of the invention to provide novel dihaloimine intermediates which can be converted to 6-methoxypenicillins and 7-methoxycephalosporins.

SUMMARY OF THE INVENTION

An imino chloride derived from a 6-acylaminopenicillin or 7-acylaminocephalosporin, such as a 6-[N(α-chloroalkenylidene)-amino]penicillanic ester, a 6-[N(α-chloro-α-arylmethylidene)-amino]-penicillanic ester, a 7-[N(α-chloroalkenylidene)amino]-cephalosporanic ester, or a 7-[N(α-chloro-α-arylmethylidene)-amino]cephalosporanic ester is allowed to react with one equivalent of strong base, such as an alkali metal amide of a secondary amine, at temperatures from −80° to −25° C. to provide an anion. A halogenating agent is added to provide a 6-halo-6-[N(α-halo-alkenylidene)amino]penicillanic ester, a 6-halo-6-[N(α-halo-α-arylmethylidene)amino]penicillanic ester, a 7-halo-7-[N(α-haloalkenylidene)amino]cephalosporanic ester, or a 7-halo-7-[N(α-halo-α-arylmethylidene)amino]cephalosporanic ester.

The 6- or 7-haloiminium halides so produced are used as intermediates in the preparation of 6-alkoxy-6-acylaminopenicillins or 7-alkoxy-7-acylaminocephalosporins. Such acylamino 6-alkoxypenicillins or 7-alkoxycephalosporins can also be converted to the 6-alkoxy-6-aminopenicillins or 7-alkoxy-7-aminocephalosporins and re-acylated to provide new acylamino derivatives.

DETAILED DESCRIPTION

The present invention provides a process for the preparation of 6-methoxypenicillins and 7-methoxycephalosporins utilizing intermediate 6-halo-6-N(α-chloroalkenylidene)-, 6-halo-6-[N(α-chlorobenzylidene)-, 6-halo-6-[N(α-chlorothenylidene)-, 6-halo-6-[N(α-chlorofurfurylidene)-, or 6-halo-6-[N(α-chloronaphthylmethylidene)amino]penicillins and corresponding 7-halo-7-[N(α-chloroalkenylidene)-, 7-halo-7-[N(α-chlorobenzylidene)-, 7-halo-7-[N(α-chlorothenylidene)-, 7-halo-7-[N(α-chlorofurfurylidene)-, or 7-halo-7-[N(α-chloronaphthylmethylidene)amino]cephalosporins represented by Formula I.

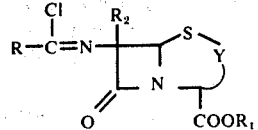

wherein R is $C_2-C_7$ 1-alkenyl, phenyl, substituted phenyl, in which the substituent is halo, $C_1-C_4$ alkoxy, nitro, $C_1-C_4$ alkyl, or phenyl, furyl, thienyl, naphthyl, styryl, or substituted styryl, in which the substituent is halo or nitro;

$R_1$ is a carboxylic acid ester forming protecting group, $R_2$ is halo,

Y is

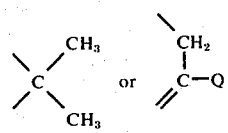

wherein Q is methyl or acetoxymethyl, with the proviso that when Y is

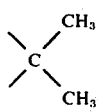

$R_2$ is other than fluoro.

The preparation of these intermediate 6-halopenicillins and 7-halocephalosporins utilizes the imino chlorides of Formula II

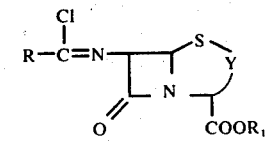

wherein R, Y, and $R_1$ are the same as above. The imino chlorides are converted to an anion of the Formula III

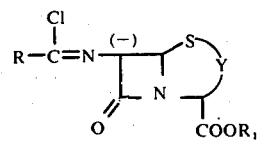

by using a strong base in an inert solvent such as tetrahydrofuran at about −80° to −25° C. The presence of the anion can be detected by the change in color of the reaction. After stirring the reaction mixture at −80° to −25° C. for 10–30 minutes, the mixture is treated with a halogenating agent in an inert solvent which can be the same as or different than above, for example, a limited amount of a polar aprotic solvent such as DMF or a solvent such as carbon tetrachloride, tetrahydrofuran, dioxane, ethylene glycol dimethyl ether, or diethylene glycol dimethyl ether.

The reaction is allowed to warm to room temperature while being stirred for about 10-60 minutes, and then the product represented by Formula II is isolated.

In the foregoing description of the process of this invention, R may not contain a replaceable hydrogen in the position $\beta$ to the nitrogen.

The term "substituted phenyl" as used herein refers to mono-, di-, tri-, and tetra-substituted phenyl wherein the substituents are the same or different. Substituents are halo, $C_1$-$C_4$ alkyl, $C_1$-$C_4$ alkoxy, nitro, or phenyl.

The term "substituted styryl" as used herein refers to mono-substituted styryl wherein the substituent is located on the phenyl portion of the styryl radical, and the substituent is nitro or halo.

The term "halo" as used herein refers to fluoro, bromo, chloro, and iodo.

The term "a carboxylic acid ester forming protecting group" as used herein refers to such ester forming groups as are commonly employed in the penicillin and cephalosporin art to protect the respective carboxylic acid functions of the penicillin and cephalosporin molecules. Illustrative of such groups are: the tetrahydropyranyl group, the trichloroethyl group employed by R. B. Woodward et al., *J. Am. Chem. Soc.*, 88, 852 1966); the p-nitrobenzyl group, U.S. Pat. No. 3,632,850; the benzhydryl(diphenylmethyl) group, British Patent No. 1,041,985; the benzyl group, U.S. Pat. No. 3,197,466; the t-butyl group, *J. Org. Chem.*, 31, 444 (1966); the p-methoxybenzyl group, R. R. Chauvette, *J. Org. Chem.*, 36, 1259 (1971); 3,5-dimethoxybenzyl group, and the phenacyl group, *J. Org. Chem.*, 29, 2006 (1964).

The identity of such ester forming carboxylic acid protecting groups, as are represented by $R_1$, is not critical in the present process and such groups serve merely to protect the carboxylic acid function so as to prevent its competition with the chlorination and displacement reactions of the present process.

The term "halogenating agent" refers to compounds which will yield a halogen to add to an imminium anion. Typical of the halogenating agents are compounds such as bromine, cyanogen bromide, N-bromosuccinimide, N-bromoacetamide, pyridinium perbromide hydrobromide, perchloryl flouride, iodine, t-butylhypochlorite, N-chlorosuccinimide, thionyl chloride, chlorine, sulfuryl chloride, and the like.

The term "strong base" is defined as any base capable of effecting abstraction of the $C_6$ or $C_7$ proton of the $\beta$-lactam ring of the penicillin or cephalosporin imine to form the anion of Formula III and at the same time are poor nucleophilic displacement agents. Strong bases which display the above-mentioned properties include alkali metal hydrides, alkali metal amides, alkali metal alkoxides, alkali metal trityl (triphenylmethyl) compounds.

The term "alkali metal" as used herein refers to lithium, sodium, or potassium.

Typical strong bases include sodium hydride, potassium t-butoxide, n-butyllithium, t-butyllithium, tritylsodium, tritylithium, tritylpotassium, potassium amide, lithium diisopropylamide, lithium N-isopropylcyclohexylamide, lithium t-butyl-t-amylamide, lithium 2,2,6,6-tetramethylpiperidide, lithium dicyclohexylamide, and the like.

A typical preparation of a compound of the invention is illustrated by the following generalized description. To a solution of diisopropylamine in dry tetrahydrofuran under nitrogen atmosphere at $-30°$ C. was added a solution of one equivalent of n-butyllithium in hexane solution. After the reaction mixture was stirred for 5 minutes, the temperature was lowered to $-78°$ C. and a solution of 2,2,2-trichloroethyl N($\alpha$-chloro-p-nitrobenzylidene) 7-aminodeacetoxycephalosporanate in dry tetrahydrofuran was added. A blue color was observed which indicated the presence of the anion. After stirring the solution 10 minutes at $-78°$ C., one equivalent of perchloryl fluoride was added as a saturated solution in dimethylformamide. The blue color was discharged almost immediately. The reaction mixture was stirred and allowed to reach $25°$ C., and after 90 minutes was diluted with a saturated aqueous solution of sodium chloride and extracted with ethyl acetate. The extract was washed and dried, and thereafter was evaporated in vacuo to yield the crude reaction product, 2,2,2-trichloroethyl 7-fluoro-7[N($\alpha$-chloro-p-nitrobenzylidene)amino]deacetoxycephalosporanate. The crude product was purified by preparative thin layer chromatography.

When larger quantities are prepared, the chromatography is preferably carried out on a column of silica gel adsorbent. The amount of dimethylformamide in the reaction mixture should be kept low to avoid by-product formation.

Following the isolation and purification of the 6- or 7- halo reaction product, it is converted into the product of Formula IV:

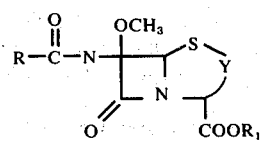

wherein R, $R_1$ and Y are the same as above.

The reaction for conversion of imino dihalides to methoxy-6-acylaminopenicillins or methoxy-7-acylaminocephalosporins of Formula IV is carried out by reacting the imino dihalide with at least one molar equivalent of methanol at $0°$-$80°$ C.

A polar cosolvent is desirable for the reaction. The polar cosolvent may be dimethyl sulfoxide or a $C_1$-$C_{10}$ carboxylic acid. Alternatively a solution of a polar organic solvent such as dimethylformamide, glyme, diglyme, etc. containing an alkyl or arylsulfonic acid can be used in combination with methanol.

The reaction time required for completion of the reaction varies from 5 minutes to 16 hours depending on the temperature of the reaction and the nature of the reactants. A halogen abstracting inorganic compound, such as silver acetate, silver nitrate, or other soluble inorganic salt which has a cation capable of reacting with halide to form an insoluble salt, can be used in combination with methanol to prepared the methoxy amide of Formula IV from the imino halide.

While we do not wish to be bound by the proposed reaction mechanism, the route of formation of the compound of Formula IV from DMSO probably proceeds as follows.

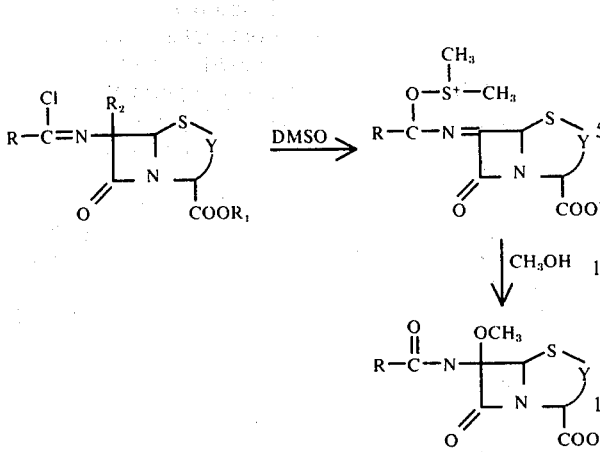

An alternate procedure for preparation of the methoxy compounds involves addition of water to the imino dihalide in DMSO or in another polar organic solvent as mentioned above in the presence of a halogen abstracting inorganic compound to yield the 6-hydroxypenicillin or 7-hydroxycephalosporin. The said hydroxy compounds can be converted to the 6-methoxy-6-acylaminopenicillins or 7-methoxy-7-acylaminocephalosporins by reaction under non-basic conditions with a methylating agent such as diazomethane or methane fluorosulfonate or the like. While one molar equivalent of water is necessary in the above reaction to generate the 6-hydroxypenicillin or 7-hydroxycephalosporin the solvents which are employed often contain sufficient water to carry the reaction to completion.

Problems are encountered with the use of any of the above conditions with the 6-fluoro-6-haloalkenylidenepenicillins because of the tendency of the compounds to undergo a rearrangement of the penicillin nucleus. Other 6-halo-6-haloalkenylidenepenicillins and 7-fluoro-7-haloalkenylidenecephalosproins behave normally and undergo the above-mentioned reactions.

Preferred reaction conditions for conversion of imino dihalides to methoxy 6-acylaminopenicillins or 7-acylaminocephalosporins of Formula IV are illustrated by the following:

2,2,2-Trichloroethyl 7-fluoro-7-[N(α-chloro-p-nitrobenzylidene)amino]deacetoxycephalosporanate was treated with refluxing 5 percent acetic acid in methanol for 15 minutes, then concentrated in vacuo to yield 2,2,2-trichloroethyl 7-methoxy-7-p-nitrobenzamidodeacetoxycephalosporanate.

The ester can be converted to the acid under appropriate known conditions such as hydrolysis or hydrogenolysis. For example, the benzyl, diphenylmethyl, p-nitrobenzyl, and 3,5-dimethoxybenzyl groups represented by $R_1$ can be removed by hydrogenolysis, for example, by reacting with hydrogen in the presence of 10 percent palladium on carbon catalyst in an inert solvent.

The 2,2,2-trichloroethyl group is removed with zinc and formic or glacial acetic acid. Other known carboxylic acid protecting groups which can be employed are removed by known methods.

Use of side chain cleavage conditions followed by reacylation as described in copending U.S. Pat. application No. 298,165 extends the utility of the present invention. According to the process of the copending patent application, 6-acylamino-6-methoxypenicillins and 7-acylamino-7-methoxycephalosporins can be converted to 6-amino-6-methoxypenicillins and 7-amino-7-methoxycephalosporins and reacted with another acid chloride to yield the desired new 6-acylamino-6-methoxypenicillin or 7-acylamino-7-methoxycephalosporin. The cleavage of the 6-acyl or 7-acyl side chain is carried out by using phosphorus pentachloride in a pyridine and chloroform solution to produce an intermediate 6-methoxy-6-iminohalide of the penicillin or 7-methoxy-7-iminohalide of the cephalosporin and treating the intermediate with an alcohol, such as methanol, under anhydrous conditions. The imino ether of the methoxy compound thus formed is then treated with additional pyridine and an excess of the desired acid chloride. The excess acid chloride is removed by reacting with an alcohol such as methanol and washing with aqueous sodium bicarbonate solution. Removal of the aqueous solvent and concentration of the organic affords the desired 6-acylamino-6-methoxypenicillin or 7-acylamino-7-methoxycephalosporin.

Illustrative of 6-halo-6-[N(α-chloro-α-arylmethylidene)amino]penicillanic esters prepared by the present invention and represented by Formula II are:

2,2,2-trichloroethyl 6-bromo-6-[N-(α-chlorobenzylidene)amino]penicillanate, 2,2,2-trichloroethyl 6-chloro-6-[N-(α-chlorobenzylidene)amino]penicillanate, 2,2,2-trichloroethyl 6-bromo-6-[N-(α-chloro-p-nitrobenzylidene)amino]penicillanate, benzyl 6-chloro-6-[N-(α-chloro-p-nitrobenzylidene)amino]penicillanate, t-butyl 6-bromo-6-[N-(α-chloro-o-nitrobenzylidene)amino]penicillanate, benzhydryl 6-bromo-6-[N-(α-chloro-m-nitrobenzylidene)amino]penicillanate, 2,2,2-trichloroethyl 6-bromo-6-[N-(αchloro-p-chlorobenzylidene)amino]penicillanate, 2,2,2-tricloroethyl 6-bromo-6-[N-(α-chlorofurfurylidene)amino]penicillanate, phenacyl 6-bromo6-[N-(α-chloro-2-thenylidene)amino]penicillanate, 2,2,2-trichloroethyl 6-bromo-6-[N-(α-chloro-2,4-dichlorobenzylidene)amino]penicillanate, benzyl 6-chloro-6-[N-(α-chloro-2,6-dimethoxybenzylidene)amino]penicillanate, 4-methoxybenzyl 6-bromo-6-[N-(α-chloro-2-chloro-3-nitrobenzylidene)amino]pencillanate, benzhydryl 6-bromo-6-[N-(α-chloro-2,4,6-tribromobenzylidene)amino]penicillanate, t-butyl 6-bromo-6-[N-(α-chloro-2,4,5-trimethylbenzylidene)amino]penicillanate, tetrahydropyranyl 6-chloro-6-[N-(α-chloro-1-naphthylmethylidene)amino]penicillanate, and the like.

Illustrative of 6-halo-6-[N-(α-chloro-2-alkenylidene)amino]penicillanic esters prepared by the present invention and represented by Formula II are:

2,2,2-trichloroethyl 6-bromo-6-[N-(α-chloro-2-propenylidene)amino]penicillanate, benzyl 6-bromo-6-[N-(α-chloro-2-heptenylidene)amino]penicillanate, and the like.

Illustrative of 6-halo-6-[N-(α-chlorocinnamylidene)amino]penicillanic esters prepared by the present invention and represented by Formula II are:

2,2,2-trichloroethyl 6-bromo-6-[N-(α-chlorocinnamylidene)amino]penicillanate, t-butyl 6-chloro-6-[N-(α-chlorocinnamylidene)amino]penicillanate, and the like.

Illustrative of 6-halo-6-[N-(α-chloro-α-arylmethylidene)amino]deacetoxycephalosporanic esters prepared by the present invention, and represented by Formula II are:

2,2,2-trichloroethyl 7-bromo-7-[N-(α-chlorobenzylidene)amino]deacetoxycephalosporanate, 4-methoxybenzyl 7-fluoro-7-[N-(α-chlorobenzylidene)amino]deacetoxycephalosporanate, tetrahydropropyranyl 7-fluoro-7-[N-(α-chlorobenzylidene)amino]deacetoxycephalosporanate, 2,2,2-trichloroethyl 7-fluoro-7-[N-(α-chloro-p-nitrobenzylidene)amino]deacetoxycephalosporanate, 2,2,2-trichloroethyl 7-bromo-7-[N-(α-chloro-p-nitrobenzylidene)amino]deacetoxycephalosporanate, 4-nitrobenzyl 7-chloro-7-[N-(α-chloro-p-nitrobenzylidene)amino]deacetoxycephalosporanate, t-butyl 7-fluoro-7-[N-(α-chloro-o-nitrobenzylidene)amino]deacetoxycephalosporanate, benzhydryl 7-bromo-7-[N-(α-chloro-m-nitrobenzylidene)amino]deacetoxycephalosporanate, 2,2,2-trichloroethyl 7-fluoro-7-[N-(α-chloro-p-chlorobenzylidene)amino]deacetoxycephalosporanate, phenacyl 7-bromo-7-[N-(α-chloro-o-chlorobenzylidene)amino]deacetoxycephalosporanate, 4-nitrobenzyl 7-chloro-7-[N-(α-chloro-m-chlorobenzylidene)amino]deacetoxycephalosporanate, 2,2,2-trichloroethyl 7-fluoro-7-[N-(α-chlorofurfurylidene)amino]deacetoxycephalosporanate, 3,5-dimethoxy 7-bromo-7-[N-(αchlorofurfurylidene)amino]deacetoxycephalosporanate, t-butyl 7-fluoro-7-[N-(α-chlorofurfurylidene)amino]deacetoxycephalosporanate, 4-methoxybenzyl 7-bromo-7-[N-(α-chloro-2-thenylidene)amino]deactoxycephalosporanate, tetrahydropyranyl 7-chloro-7-[N-(α-chloro-2-bromo-3-chlorobenzylidene)amino]deacetoxycephalosporanate, t-butyl 7-fluoro-7-[N-(α-chloro-3-bromo-4-nitrobenzylidene)amino]deacetoxycephalosporanate, benzhydryl 7-bromo-7-[N-(α-chloro-3,5-dibromobenzylidene)amino]deacetoxycephalosporanate, 2,2,2-trichloroethyl 7-fluoro-7-[N-(α-chloro-2,4-dinitrobenzylidene)amino]deacetoxycephalosporanate, tetrahydropyranyl 7-bromo-7-[N-(α-chloro-2,4,6-trichlorobenzylidene)amino]deacetoxycephalosporanate, 4-nitrobenzyl 7-chloro-7-[N-(α-chloro-2,4,5-trimethylbenzylidene)amino]deacetoxycephalosporanate, 4-methoxybenzyl 7-iodo-7-[N-(α-chloro-3,4,5-triiodobenzylidene)amino]deacetoxycephalosporanate, 2,2,2-trichloroethyl 7-fluoro-7-[N-(α-chloro-2,3,4,5,-tetrachlorobenzylidene)amino]deacetoxycephalosporanate, phenacyl 7-bromo-7-[N-(α-chloro-1-naphthylmethylidene)amino]deacetoxycephalosporanate, benzhydryl 7-iodo-7-[N-(α-chloro-5-chloro-2-naphthylmethylidene)amino]deacetoxycephalosporanate, tetrahydropyranyl 7-bromo-7-[N-(α-chloro-4-phenylbenzylidene)amino]deacetoxycephalosporanate, and the like.

Illustrative of 7-halo-7-[N-(α-chloro-2-alkenylidene)amino]deacetoxycephalosporanic esters prepared by the present invention and represented by Formula II are:

2,2,2-trichloroethyl 7-fluoro-7-[N-(α-chloro-2-propenylidene)amino]deacetoxycephalosporanate, benzyl 7-bromo-7-[N-(α-chloro-2-hexenylidene)amino]deacetoxycaphalosporanate, benzhydryl 7-fluoro-7-[N-(α-chloro-2-heptenylidene)amino]deacetoxycephalosporanate, and the like.

Illustrative of 7-halo-7-[N-(α-chlorocinnamylidene)amino]cephalosporanic esters prepared by the present invention and represented by Formula II are:

2,2,2-trichloroethyl 7-bromo-7-[N-(α-chloro-p-chlorocinnamylidene)amino]deacetoxycephalosporanate, phenacyl 7-fluoro-7-[N-(α-chloro-o-nitro-cinnamylidene)amino]deacetoxycephalosporanate, and the like.

Illustrative of 7-halo-7-[N-(α-chloro-α-arylmethylidene)amino]cephalosporanic esters prepared by the present invention and represented by Formula II are:

2,2,2-trichloroethyl 7-bromo-7-[N-(α-chlorobenzylidene)amino]cephalosporanate, benzyl 7-fluoro-7-[N-(α-chloro-p-nitrobenzylidene)amino]cephalosporanate, t-butyl 7-chloro-7-[N-(α-chloro-m-chlorobenzylidene)amino]cephalosporanate, 4-methoxybenzyl 7-fluoro-7-[N-(α-chlorofurfurylidene)amino]cephalosporanate, and the like.

Illustrative of 7-halo-7-[N-(α-chloro-2-alkenylidene)amino]cephalosporanic esters and represented by Formula II are:

tetrahydropyranyl 7-fluoro-7-[N-(α-chloro-2-propenylidene)amino]cephalosporanate, 4-nitrobenzyl 7-bromo-7-[N-(α-chloro-2-heptenylidene)amino]cephalosporanate, and the like.

Illustrative of 7-halo-7-[N-(α-chlorocinnamylidene)amino]cephalosporanic esters and represented by Formula II are:

4-methoxybenzyl 7-chloro-7-[N-(α-chlorocinnamylidene)amino]cephalosporanate, and the like.

Starting materials for the process of this invention can be prepared by treating the appropriate acylamino penicillin or cephalosporin ester with phosphorus pentachloride in the presence of a hydrogen chloride scavenger, such as pyridine, in an appropriate non-reactive solvent, such as methylene chloride. After the reaction mixture is cooled to −20° to −80° C., an alcohol such as methanol is added. After being stirred at this temperature for 5–30 minutes, the reaction mixture is diluted with an appropriate extracting solvent, such as methylene chloride, and washed well with aqueous saturated sodium chloride solution. After drying and concentrating the extract to a small volume in vacuo, an appropriate non-polar crystallizing solvent such as diethyl ether is added to yield the 6-[N-(α-chloro-2-alkenylidene)amino]penicillanic ester or 7-[N-(α-chloro-2-alkenylidene)amino]cephalosporanic ester.

Preparation of Imino Chloride

Eight and seventy-nine hundredths grams of 2,2,2-trichloroethyl N-furoyl-7-aminodeacetoxycephalosporanate was dissolved in 100 ml. of methylene chloride, and 2 ml. of pyridine was added. Four and sixty-two hundredths grams of phosphorus pentachloride was added, and the reaction mixture was stirred at 25° C. for 15 minutes. The reaction temperature was lowered to −20° C., and 10 ml. of methanol was added. After being stirred 5 minutes at −20° C., the reaction mixture was diluted with 100 ml. of methylene chloride, washed twice with 600 ml. portions of saturated aqueous sodium chloride solution and then dried over magnesium sulfate. The solvent was concentrated in vacuo until the product crystallized, then 300 ml. of ethyl ether was added. The product was filtered, giving 4.83 g. of 2,2,2-trichloroethyl 7-[N-(α-chlorofurfurylidene)amino]-deacetoxycephalosporanate.

EXAMPLE 1

To a solution of 0.78 ml. of diisopropylamine in 30 ml. of dry tetrahydrofuran under nitrogen atmosphere at −20° C. was added 3 ml. of 1.6 M n-butyllithium in hexane solution. After stirring this lithium diisopropylamide solution 5 minutes, the temperature was lowered to −78° C., and a solution of 2.57 g. of 2,2,2-trichloroethyl 7-[N-(α-chloro-p-nitrobenzylidene)amino]deacetoxycephalosporanate in 30 ml. of tetrahydrofuran was added. After stirring this solution of the anion 10 minutes at −78° C., 0.51 g. of perchloryl fluoride was added as a saturated solution in 105 ml. of dimethylformamide. The reaction mixture was allowed to warm to room temperature and, after 90 minutes, the mixture was added to 500 ml. of saturated aqueous sodium chloride solution. Three hundred milliliters of ethyl acetate was added and the ethyl acetate layer was separated and washed three times with 500 ml. portions of aqueous sodium chloride solution. After the organic solution was dried over magnesium sulfate, the solvent was removed in vacuo. The 2,2,2-trichloroethyl 7-fluoro-7-[N-(α-chloro-p-nitrobenzylidene)amino]deacetoxycephalosporanate was separated by preparative thin layer chromatography. The first fraction contained 364 mg. of pure product. The NMR spectrum confirmed the structure.

EXAMPLE 2

A 5 mM solution of lithium diisopropylamide was prepared as in Example 1, and a solution of 2.34 g. of 2,2,2-trichloroethyl 7-[N-(α-chlorobenzylidene)amino]deacetoxycephalosporanate in 30 ml. of tetrahydrofuran was added at −78° C. Fifty-three hundredths grams of cyanogen bromide in 20 ml. of dimethylformamide was added, and the reaction mixture was stirred 30 minutes. The product, 2,2,2-trichloroethyl 7-bromo-7-[N-(α-chlorobenzylidene)amino]deacetoxycephalosporanate, was isolated as described in Example 1.

EXAMPLE 3

The anion from 2.57 g of 2,2,2-trichloroethyl 7-[N-(α-chloro-p-nitrobenzylidene)amino]deacetoxycephalosporanate was prepared using the procedure of Example 1. To the solution containing the anion was added (at −78° C.) .27 ml. of bromine in 30 ml. of carbon tetrachloride. The isolation of the product was carried out as in Example 1 and yielded 1.45 g. of 2,2,2-trichloroethyl 7-bromo-7-[N-(α-chloro-p-nitrobenzylidene)amino]deacetoxycephalosporanate which gave the correct NMR spectrum.

EXAMPLE 4

Two and twenty-nine hundredths grams of 2,2,2-trichloroethyl 7-[N-(α-chlorofurfurylidene)amino]-deacetoxycephalosporanate was dissolved in 30 ml. of tetrahydrofuran and added to 50 ml. of tetrahydrofuran solution containing one equivalent of lithium diisopropylamide prepared as in Example 1. Fifty-one hundredths grams of perchloryl fluoride in dimethylformamide was added, and the product was isolated as in Example 1. The product, 2,2,2-trichloroethyl 7-fluoro-7-[N-(α-chlorofurfurylidene)amino]deacetoxycephalosporanate, was purified by thin layer chromatography to give 518 mg. of pure product. NMR and IR spectra were correct for the structure.

EXAMPLE 5

Four and seventy-three hundredths grams of p-nitrobenzyl 7-[N-(α-chlorobenzylidene)amino]penicillanate in 60 ml. of tetrahydrofuran was added to a solution of 10 mM of lithium diisopropylamide as in Example 1. To this solution at −78° C., 0.54 ml. of bromine in 30 ml. of carbon tetrachloride was added. After 5 minutes the product was isolated as in Example 1. The product, p-nitrobenzyl 6-bromo-6-[N-(α-chlorobenzylidene)amino]penicillanate, was purified by preparative thin layer chromatography: yield 676 mg. The product was crystallized from ethyl acetate and hexane solution.

Analysis: Calc. for $C_{22}H_{19}ClBrN_3O_5S$
(percent): C, 47.80; H, 3.46; N, 7.60; S, 5.80.
Found (percent): C, 48.02; H, 3.52; N, 7.83; S, 5.64.

EXAMPLE 6

Two and nine hundredths grams of 2,2,2-trichloroethyl 7-[N-(α-chloro-2-propenylidene)amino]-deacetoxycephalosporanate in 30 ml. of tetrahydrofuran was added to a 5 mM solution of lithium diisopropylamide as in Example 1. Fifty-one hundredths grams of perchloryl fluoride was added added and the product was isolated as in Example 1. Purification by preparative thin layer chromatography gave 164 mg. of 2,2,2-trichloroethyl 7-fluoro-7-[N-(α-chloro-2-propenylidene)amino]deacetoxycephalosporanate.

EXAMPLE 7

Two and forty-seven hundredths grams of 2,2,2-trichloroethyl 7-[N-(α-chlorocinnamylidene)amino]-deacetoxycephalosporanate was dissolved in 30 ml. of tetrahydrofuran and added to a solution of 5 mM of lithium diisopropylamide. Fifty-one hundredths grams of perchloryl fluoride was added at −78° C., and the product was isolated as in Example 1. Following preparative thin layer chromatography, 432 mg. of 2,2,2-trichloroethyl 7-fluoro-7-[N-(α-chlorocinnamylidene)amino]deacetoxycephalosporanate was isolated as in Example 1.

EXAMPLE 8

The product of Example 1 was treated with refluxing 5 percent acetic acid in methanol for 15 minutes. A substantial amount of 2,2,2-trichloroethyl 7-methoxy-7-p-nitrobenzamidodeacetoxycephalosporanate was isolated by evaporating the methanol and acetic acid solution.

EXAMPLE 9

Five hundred and fifty-two thousandths grams of the product from Example 5 was dissolved in a mixture of 10 ml. of methanol and 10 ml. of dimethyl sulfoxide. After being stirred at 25° C. for 16 hours, the solution containing the product was diluted with ethyl acetate and washed with saturated aqueous sodium chloride solution. The organic material was concentrated in vacuo, purified by preparative thin layer chromatography and identified as 6-methoxy-6-benzamidopenicillanic acid.

EXAMPLE 10

2,2,2-Trichloroethyl 7-[N-(α-bromocinnamylidene)amino]deacetoxycephalosporanate (2.48 g.) was brominated by the method of Example 2 to yield 1.2 g. of 2,2,2-trichloroethyl 7-bromo-7-[N-(α-bromocinnamylidene)amino]deacetoxycephalosporanate. Four hundred milligrams of the dibromo compound was dissolved in 10 ml. of wet dimethyl sulfoxide and allowed to stand at 25° C. for 14 hours. The solvent was removed in vacuo, and the product was isolated by preparative thin layer chromatography to yield 70 mg. of 2,2,2-trichloroethyl 7-hydroxy-7-cinnamamidodeacetoxycephalosporanate. The elemental analysis of this compound shows that there is no bromine present.

A solution of 70 mg. of the hydroxy compound in 50 ml. of methylene chloride at 0° C. was treated with a few drops of boron trifluoride etherate and 20 ml. of a solution of 1.5 mg./ml. of diazomethane in diethyl ether. The reaction mixture was stirred for 40 min. at 0° C. and 1 ml. of acetic acid was added. The solvent was evaporated in vacuo. The residue was dissolved in ethyl acetate and the solution was dried. The material was placed on a silica gel preparative plate in a solvent system of 40% ethyl acetate in hexane. Eight milligrams of material was isolated which gave correct N.M.R. and mass spectral data for 2,2,2-trichloroethyl 7-methoxy-7-cinnamamidodeacetoxycephalosporanate.

I claim:

1. A compound of the formula

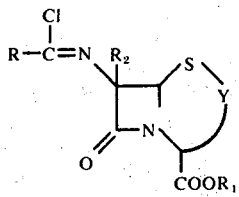

wherein
R is $C_2$-$C_7$ 1-alkenyl; phenyl; substituted phenyl, in which the substituent is halo, $C_1$-$C_4$ alkoxy, nitro, $C_1$-$C_4$ alkyl, or phenyl; furyl; thienyl; naphthyl; styryl; or substituted styryl, in which the substituent is halo or nitro;
$R_1$ is a carboxyl protecting ester forming group;
$R_2$ is halo;
Y is:

Wherein Q is methyl or acetoxymethyl.

2. The compound of claim 1 in which $R_1$ is 2,2,2-trichloroethyl, p-nitrobenzyl, benzhydryl, benzyl, t-butyl, p-methoxybenzyl, 3,5-dimethoxybenzyl, tetrahydropyranyl, or phenacyl.

3. The compound of claim 2 wherein $R_2$ is fluoro.

4. The compound of claim 3, said compound being 2,2,2-trichloroethyl 7-fluoro-7-[N-(α)-chloro-p-nitrobenzylidene)amino]deacetoxycephalosporanate.

* * * * *